United States Patent [19]

Hanlon et al.

[11] Patent Number: 5,229,267
[45] Date of Patent: Jul. 20, 1993

[54] ASSAY FOR EVALUATING INHIBITION OF PMN ELASTASE BY N-SUBSTITUTED AZETIDINONES

[75] Inventors: William A. Hanlon, Lebanon; John L. Humes, Berkeley Heights; Wilson B. Knight, Watchung; Richard A. Mumford, Red Bank, all of N.J.

[73] Assignee: Merck & Co., Inc., Rahway, N.J.

[21] Appl. No.: 750,147

[22] Filed: Aug. 26, 1991

[51] Int. Cl.$^5$ .......................... C12Q 1/37; C12Q 9/66; G01N 33/53; C12N 9/99
[52] U.S. Cl. ..................................... 435/7.4; 435/18; 435/23; 435/218; 435/184
[58] Field of Search .................. 435/7.4, 7.71, 18, 218, 435/183, 23, 184; 424/9

[56] References Cited

U.S. PATENT DOCUMENTS

| 4,596,768 | 6/1986 | Singh et al. | 435/7 |
| 4,680,391 | 7/1987 | Firestone et al. | 540/355 |

FOREIGN PATENT DOCUMENTS

| 0038935 | 3/1981 | European Pat. Off. |
| 0199630 | 10/1986 | European Pat. Off. |
| 0337549 | 10/1989 | European Pat. Off. |

OTHER PUBLICATIONS

Firestone et al Tetrahedron 46 #7 pp. 2255–2262 (1990).
Ashe et al. JBC 256 #22 pp. 11603–11606 (1981).
Levilliers Arch. Biochem. Biophy. 140, 474–483 (1970).
Jaenicke et al in *Protein Structure a Practical Approach* pp. 191–223 (1990).
Colman in *Protein Function A Practical Approach* pp. 77–99 (1990).
Rando Meth. Enz. 46 pp. 28–41 (1977).
Chem Abstracts, vol. 78, No. 17, 30 Apr. 1973.
Chem Abstracts, vol. 115, No. 13, 30 Sep. 1991.

*Primary Examiner*—Esther L. Kepplinger
*Assistant Examiner*—Lora M. Green
*Attorney, Agent, or Firm*—Curtis C. Panzer; Raymond M. Speer

[57] ABSTRACT

N-substituted azetidinones are a class of inhibitors of human leukocytes elastase which are known to be useful in the treatment of a wide variety of antiinflammatory and antidegenerative diseases. In inhibiting elastase, the therapeutic agents are shown to form a characteristic stable complex with the enzyme. In the assay disclosed herein, the inhibitor-enzyme complex is advantageously hydrolyzed and specific product(s) of the hydrolysis are measured. The assays are useful in a clinical setting, for determining appropriate dosage and assessing the effectiveness of treatment.

12 Claims, 2 Drawing Sheets

ASSAY FOR EVALUATING INHIBITION OF PMN ELASTASE BY N-SUBSTITUTED AZETIDINONES

BACKGROUND OF THE INVENTION

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, glomercular nephritis, osteoarthritis, spondylitis, lupus, psoriasis, atherosclerosis, sepsis, septicemia, shock, periodontitis, cystic fibrosis, myocardial infarction, reperfusion injury, meningitis, glomerulonephritis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am.* July 1974, pp. 74–88). For example, one of the natural inhibitors, $\alpha_1$-Antitrypsin, is a glycoprotein contained in human serum that has a wide inhibitory spectrum covering, among other enzymes, elastase both from PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes. This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, New York, pp. 196–206, 1979.

A number of low molecular weight inhibitors of HLE have been reported. See, for example, Stein, R. L., Trainor, D. A. & Wildonger, R. A. (1985) in *Annual Reports in Medicinal Chemistry*, ed. Egan (Academic Press), Vol. 20, pp. 237–246; Doherty, J. B., Ashe, B. M., Argenbright, L. W., Barker, P. L., Bonney, R. J., Chandler, G. O., Dahlgren, M. E., Dorn, C. P., Finke, P. E., Firestone, R. A. Fletcher, D., Hagmann, W. K., Mumford, R., O'Grady, L., Maycock, A. L., Pisano, J. M., Shah, S. K., Thompson, K. R. & Zimmerman, M. (1986) *Nature* 322, 192–194; Firestone, R. A., Barker, P. L., Pisano, J. M., Ashe, B. M. & Dahlgren, M. E..(1990) *Tetrahedron*, 46, pp 2255. See also European Application Publication EP 0 337 549, published Oct. 18, 1989.

Treatment of HLE mediated diseases by administration of HLE inhibitors has been previously described. See also European Application Publication EP 0 337 549, published Oct. 18, 1989. Treatment with a therapeutic agent is affected through the inhibition of HLE achieved through the formation of an HLE-inhibitor complex.

SUMMARY OF THE INVENTION

N-substituted azetidinones are a class of inhibitors of human leukocytes elastase which are known to be useful in the treatment of a wide variety of antiinflammatory and antidegenerative diseases. In inhibiting elastase, the therapeutic agents are shown to form a characteristic stable complex with the enzyme. In the assays disclosed herein, the inhibitor-enzyme complex is advantageously hydrolyzed and specific product(s) of the hydrolysis are measured. The assays are useful in a clinical setting, for determining appropriate dosage and assessing the effectiveness of treatment.

DETAILED DESCRIPTION OF THE INVENTION

Figure 1:
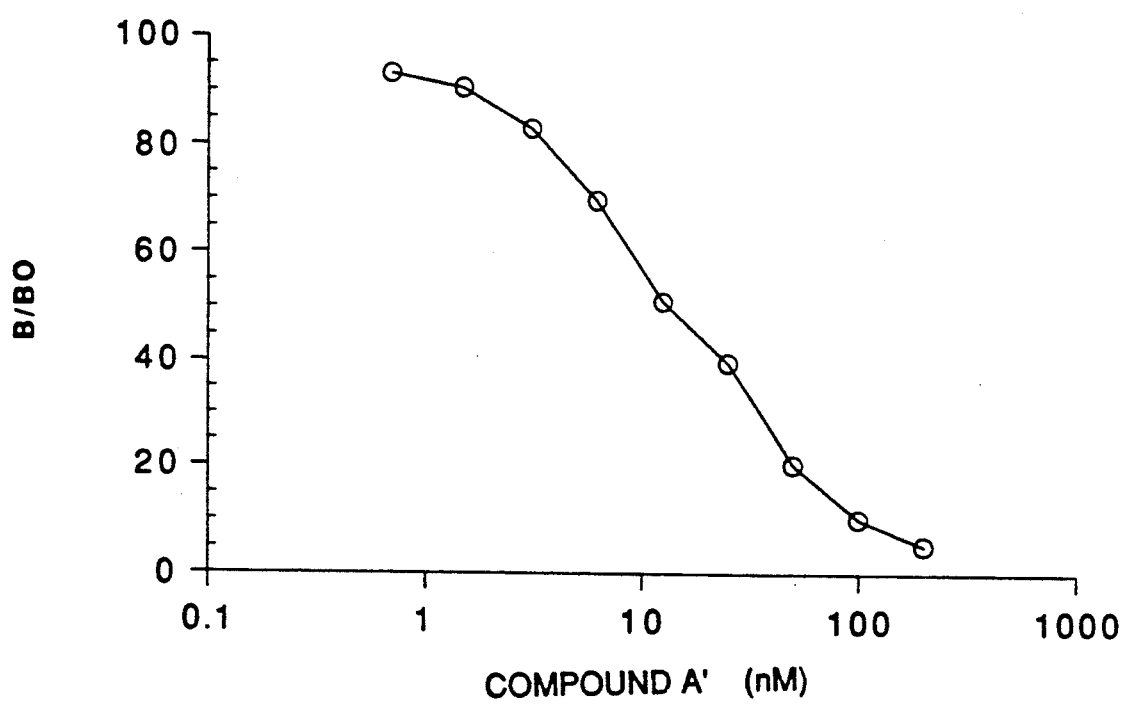
FIG. 1 depicts the binding of Compound A' incubated with $^3$H-Compound A' and antibody R674; total binding (BO) is the number of dpm (decompositions per minute) bound to the antibody in the absence of unlabeled Compound A', and displaced binding (B) is the number of dpm bound to the antibody in the presence of Compound A'.

In one embodiment, the invention concerns an assay for quantitatively measuring the inhibition of human leukocyte elastase (HLE) by N-substituted azetidinones wherein said inhibition is the result of the formation of an HLE-inhibitor complex comprising:

(a) hydrolyzing the HLE-inhibitor, complex, and
(b) measuring the amount of one or more of the products of Step (a).

Treatment of HLE mediated diseases by administration of HLE inhibitors has been previously described. See also European Application Publication EP 0 337 549, published Oct. 18, 1989. Treatment with a therapeutic agent is affected through the inhibition of HLE achieved through the formation of an HLE-inhibitor complex.

This complex will be hereinafter described as HLE-I complex. This complex has essentially the same character as a classical covalent substrate-enzyme interaction.

The overall reaction of an inhibiting agent with HLE can be summarized by the sequences:

$$I + HLE \xrightarrow{(association)} HLE\text{-}I \xrightarrow{(dissociation)} HLE + P_i$$

That is, the association of HLE with an inhibiting agent results in a stable complex, namely, HLE-I, which complex can later dissociate into one or more products $P_i$ plus regenerated active or inactive HLE.

For example, treatment with inhibiting agents A and B results in association complexes HLE-A and HLE-B respectively, which upon dissociation yield respectively dissociated products A' and B' as shown below:

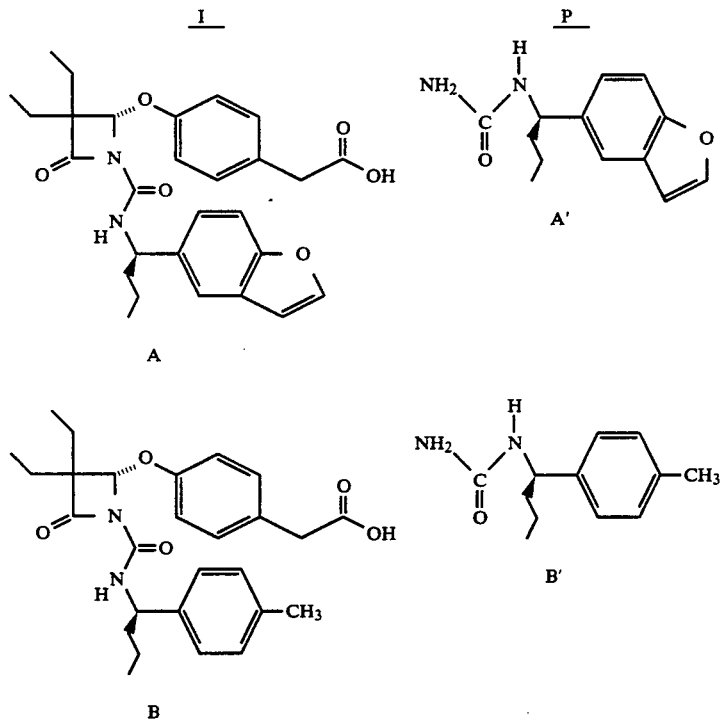

Applicants have found that when and if the HLE-I complex is stable such as upon treatment with an irreversible inhibitor, the amount of HLE-I present in a bodily fluid such as saliva, urine, blood, synovial fluid, serum, sputum or mucous secretions and bronchial alveolar lavage fluid can be quantitatively measured.

With specific regard to the azetidinones of Formula I, $$\underset{O}{\overset{R^1}{\underset{|}{R-}}}\overset{Z_2}{\underset{|}{\phantom{C}}}\overset{O}{\underset{\|}{C}}-\overset{H}{\underset{|}{N}}-\overset{H}{\underset{|}{C}}-Z_1 \quad\quad I$$
(structure I, with M below C)

applicants have found that treatment with the active agent in vivo, results in inhibition of HLE via the formation of a stable association complex of HLE and said active agent.

These complexes have been found to be quite stable, with halftimes of dissociation at pH 7.5 and 37° C. often in excess of 10 hours.

This HLE-I association complex dissociates to regenerate active enzyme and certain drug related products. The applicants have surprisingly found that characteristic of such a dissociation reaction is the stoichiometric production of an inhibitor related product corresponding to the urea derived from the nitrogen of the β-lactam. For example, a complexed inhibiting agent of formula I $$\text{(Formula I)} \quad\quad I$$

wherein
R and $R^1$ are each individually ethyl;
M is allyl or n-propyl,
$Z_1$ is
(a) 5-benzofuranyl or
(b) substituted phenyl wherein the substituent is methyl or ethoxy; and
$Z_2$ is a leaving group such as substituted phenoxy wherein the substituent is $$-\overset{O}{\underset{\|}{C}}-OH \quad \text{or} \quad -CH_2-\overset{O}{\underset{\|}{C}}OH,$$

upon dissociation will yield HLE, and a dissociation product of formula II $$H_2N-\overset{O}{\underset{\|}{C}}-\overset{H}{\underset{|}{N}}-\overset{H}{\underset{|}{\underset{M}{C}}}-Z_1 \quad\quad II$$

In one embodiment the invention concerns a method for determining the amount of HLE-I association complex formed by administration of a β-lactam inhibitor of formula I $$\text{(Formula I)} \quad\quad I$$

wherein
R and $R^1$ are each individually ethyl;
M is allyl or n-propyl
$Z_1$ is
(a) 5-benzofuranyl or
(b) substituted phenyl wherein the substituent is methyl or ethoxy; and
$Z_2$ is substituted phenoxy wherein the substituent is $$-\overset{O}{\underset{\|}{C}}-OH \quad \text{or} \quad -CH_2-\overset{O}{\underset{\|}{C}}OH$$

comprising:
(a) incubating HLE with a compound of formula I to yield an HLE-I association complex;
(b) extracting HLE-I association complex from the said incubated sample;
(c) dissociating said HLE-I complex to yield a product of formula II $$H_2N-\overset{O}{\underset{\|}{C}}-\overset{H}{\underset{|}{N}}-\overset{H}{\underset{|}{\underset{M}{C}}}-Z_1 \quad\quad II$$

and
(d) determining, quantitatively, the amount of compound of formula II produced.

The amount of formula II produced can be determined by chromatographic means such as HPLC, TLC and spectral absorbance. Additionally, the compounds can be measured by mass spectrometry. Incubation of a sample may be achieved by heat treating or treating with agents such as necleophiles or denaturing agents such as guanadinum chloride. Extracting of the HLE-I association complex may be achieved in various organic solvents including diethyl ether, methylene chloride, ethyl acetate, or water saturated ethyl acetate.

Typically the samples are extracted up to three times with 5 volumes of water saturated ethyl acetate in order to remove uncomplexed/free compound of formula I. The organic phase is discarded, the aqueous phase is adjusted to a volume of about two ml with PBS, the adjusted aqueous phase is heated for approximately two hours in a closed tube (to prevent evaporation) in order to convert the HLE-I complex to yield compound of formula II. The heated aqueous phase is treated with a roughly equal volume of acetonitrile, vortexed and centrifuged at 1300×g for about 15 minutes to remove insoluble materials. The insoluble materials pellet is washed with an additional 2 mls of acetonitrile, vortexed and centrifuged as above. The acetonitrile phases are combined and evaporated to dryness under nitrogen. The residue is disolved in PET/GEL buffer for determination of formula II concentration by RIA.

Dissociation of the HLE-I complex may be achieved by heating the complex at 30° to 100° C., or more at, for example, pH 2 to 10 for 1 to 100 minutes or more, depending on the stability of the HLE-I complex. Alternatively, dissociation may be achieved by treating with agents such as nucleophiles or denaturing agents or solvents. The HLE-I complex can be advantageously dissociated by boiling preferably for 2 hours under neutral conditions. Applicants have found it is advantageous to remove free (un-complexed) inhibitor prior to boiling.

The amount of Formula II can be advantageously determined by radioimmune assay (RIA). This method relies upon the use of an antibody specific against the compound of formula II. Immunogens are prepared by attaching the individual compound of formula II to an immunogenic carrier molecule capable of inducing antibody synthesis in animals. An immunogen is defined herein as a substance of sufficient size that when introduced into an animal, it stimulates the production of antibodies reactive with the specific antigen or epitope. Immunogenic carrier is defined herein as a protein or other high molecular weight compound to which an antigen or epitope is conjugated in vitro and which renders the antigen or epitope capable of stimulating an immune response.

In the method a sample containing a unknown level of compound of formula II, is incubated with a known amount of compound of formula II, in the presence of an antibody which is specific against the compound of radiolabelled formula II, as described above.

Monospecific antibodies to compounds of formula II are purified from mammalian antisera containing antibodies reactive against both the peptides and the carrier or prepared as monoclonal antibodies reactive with only the compound of formula II using the technique of Kohler and Milstein, Nature 256:495–497 (1975). Monospecific antibody as used herein is defined as a single antibody species or multiple antibody species with homogenous binding characteristics for the formula II antigen. Homogenous binding as used herein refers to the ability of the antibody species to bind to a specific antigen or epitope, such as that of formula II. The monospecific antibody of the present disclosure includes, but is not limited to, the following isotypes: IgA, IgG, IgM and all subclasses of these isotypes. The monospecific antibody includes either kappa or lambda light chains and variable region groups and subgroups that react with the epitopes, antigens or immunogens described herein. Formula II specific antibodies are raised by immunizing animals such as mice, rats, guinea pigs, rabbits, goats and horses, with rabbits and guinea pigs being preferred, with an appropriate concentration of the specific carrier linked compound of formula II, either with or without an immune adjuvant. Preimmune serum is collected prior to the first immunization. Each animal receives between 1 to 50 ug and about 300 mg of a single peptide-carrier complex associated with an acceptable immune adjuvant. Such acceptable adjuvants include, but are not limited to Freund's complete, Freund's incomplete, alum-precipitate, water in oil emulsion containing Corynebacterium parvum and tRNA. The initial immunization consisted of the formula II-carrier conjugate in, preferably, Freund's complete adjuvant at multiple sites either subcutaneously or intradermally. Each animal is bled at regular intervals, preferably 10 to 14 days following a boost, to determine antibody titer. The animals may or may not receive booster injections following the initial immunization. Those animals receiving booster injections are given an equal amount of formula II-carrier conjugate in Freund's incomplete adjuvant by the same route. Booster injections are given at about four week intervals until maximal titer is obtained. At about 10 to 14 days after each booster immunization or about weekly after a single immunization, the animals are bled, the serum collected, aliquoted and stored at about −20° C.

Monoclonal antibodies (mAb) reactive with the formula II antigens are prepared by immunizing inbred mice preferably Balb/c with the appropriate peptide-conjugate. The mice are immunized by the intraperitoneal or subcutaneous route with about 0.1 mg to about 10 mg, preferably about 1 mg, of the specific antigenic peptide conjugate in about 0.5 ml buffer or saline incorporated in an equal volume of an acceptable adjuvant. Such acceptable adjuvants include, but are not limited to, Freund's complete, Freund's incomplete, alum-precipitate, water-in-oil emulsion containing Corynebacterium parvum and t-RNA, with Freund's incomplete adjuvant (IFA) being preferred. The mice received an initial immunization on day 0 and are rested for approximately 24 weeks. Immunized mice are given a booster immunization of about 1 mg of the conjugate or peptide in a buffer solution such as phosphate buffered saline by the intravenous route. At approximately day three after the booster immunization the mice are tested for peptide antibody. Lymphocytes, from antibody positive mice, preferably splenic lymphocytes, are obtained by removing spleens from immunized mice by standard procedures known to the art. Hybridoma cells are produced by mixing the splenic lymphocytes with an appropriate fusion partner under conditions which will allow the formation of stable hybridomas. Fusion partners may include, but are not limited to: mouse myelomas P3-NS1-Ag 4-1; MPC-11; S-194; NS..1 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented DULBECCO's MODIFIED EAGLES MEDIUM (DMEM) by procedures known in the art. Supernatants are collected from growth positive wells on about days 14, 18 and 21 and are screened for antibody production by a solid phase immunoradioassay (SPIRA) using the specific peptide antigens as the antigen. The culture supernates are also tested in the Ouchterlony precipitin assay to determine the isotype of the mAb. Cells from the antibody positive wells are cloned in soft agar by the technique of MACPHERSON, SOFT AGAR TECHNIQUES, in Tissue Culture Methods and Applications, Kruse and Paterson. Eds Academic Press, 1973.

As may be appreciated by those of skill in the art, the invention herein described encompassed not only the antibodies specifically produced, but also the antibody fragments including the F(ab')$_2$, the Fab and any other fragments that can bind the compounds of formula II.

Monoclonal antibodies are produced in vivo by injecting pristane primed BALB/c mice, approximately 0.5 ml per mouse, with about $2 \times 10^6$ to about $6 \times 10^6$ hybridoma cells, about 4 days after priming. Ascites fluid is collected at approximately 8–12 days and the monoclonal antibodies precipitated with ammonium sulfate, about 35% to about 60% of saturation, with 45% being preferred, washed and resuspended in a physiologically acceptable buffer at a pH of about 7.2. Such physiologically acceptable buffers include, but are not limited to, phosphate buffered saline, phosphate buffered saline glucose, buffered saline and the like.

In vitro production of anti-formula II mAb is carried out by growing the hybridoma in DMEM containing about 2% fetal calf serum to obtain sufficient quantities. The in vitro produced mAb is purified by the same procedure as that for the ascites fluid. The monoclonal antibodies are further purified by affinity chromatography using a protein A SEPHAROSE matrix and the technique of Ey et al., Immunochemistry 15:429–436 (1978) for IgG antibodies or a similar technique for other antibody isotypes. The purified monoclonal antibody, is neutralized with about 1M phosphate buffer at about pH 8.0 and stored as above.

Antibody titers of animal sera or monoclonal antibodies, antibody sensitivity, antibody specificity and the presence of and concentration of unknown antigens in body fluids are determined by various serological or immunological assays including precipitation, passive agglutination, enzyme-linked immunosorbent antibody (ELISA) technique, and radioimmunoassay (RIA) with RIA being preferred. Titer is defined herein as a measure of the concentration of antibody in a serum sample. The antibody titer of a given serum sample is related to the affinity of the antibody for the antigen. A serological or immunological assay is defined as a method of determining a specific component of a mixture or a specific amount of a known substance in which specific antigens or antibodies are used for the determination. Each assay includes the appropriate controls. The RIA is carried out in an assay buffer which may include, but is not limited to, buffered saline, phosphate buffer, phosphate buffered saline, DULBECCO's phosphate buffered saline, DULBECCO's calcium-and-magnesium-free buffered saline with DULBECCO's calcium-and-magnesium-free phosphate buffered saline (GIBCO) being preferred. The assay buffer may be used alone or preferably supplemented with about 0.1% gelatin, about 0.01% thimerasol and 1.0 mM ethylenediaminetetraacetic acid (EDTA). Antiserum or monoclonal antibodies are prepared for antibody titer determination by dilution in the assay buffer. The initial dilutions are generally 1:1,000, 1:5,000 and 1:10,000.

Antigenic probes useful for antibody binding and titer determination include either synthesized or native specific antigen of formula II. Probes are selected or designed to be easily attached to a label or a tracer such as enzymes, fluorescent dyes, radioisotopes or haptens. The tracer or label allows for quantification of the serologic reaction. Radioisotopes are the preferred label or tracer for the embodiments of this invention. Probe peptides are labeled with tritium ($^3H$), $^{14}$carbon ($^{14}C$), $^{125}$iodine ($^{125}I$) or $^{131}I$, with $^3H$ being preferred.

The radioactive probe is diluted in assay buffer to yield about 10,000 counts per minute (cpm) to about 30,000 cpm per aliquot, with about 20,000 cpm being preferred. The appropriate concentration of the specific probe is contacted with the diluted antibody. All determinations are made in duplicate. Following the contacting of the diluted antibody with the labeled probe, the mixture is incubated at about 4° C. for about 10 to about 20 hours. Non-antibody-bound radioactive probe is removed from the reaction mixture by chromatographic, precipitation, immunoprecipitation or adsorption techniques with adsorption of the unbound probe onto dextran-coated activated charcoal being preferred. The dextran-coated charcoal is prepared by suspending activated charcoal, USP, at about 3% (w/v) in 10 mM phosphate buffer, pH 7.5, containing about 0.25% (w/v) dextran, about 60,000 to about 90,000 average mol. wt., with about 70,000 average mol. wt. being preferred. The dextran-charcoal mixture is allowed to stand overnight, sedimented by centrifugation, washed once in dextran-containing phosphate buffer as above and centrifuged again. The dextran-coated activated charcoal is resuspended in the same buffer about to a 3% concentration. Immediately before use in the assay, the dextran-coated activated charcoal is diluted about 10-fold in DULBECCO's PBS and an amount sufficient to bind free probe is added to each sample. After a brief incubation period in a slurry of ice in water, the charcoal is sedimented by centrifugation and the supernatant fluid collected and counted in a gamma counter. Each assay includes charcoal-free controls, to which about 1 ml of PBS is added, for determination of total counts, and antibody-free controls for determination of non-specific binding. Percent specific binding at each antiserum dilution is determined by subtracting the value for non-specific binding from the value of antiserum binding and then dividing by the total counts per minute.

Sensitivity of the antisera is also determined by serologic assays, with RIA being preferred. The antiserum is diluted in an appropriate buffer, such as assay buffer, such that it binds about 15 percent to about 40 percent of the total radioactive probe, with about 25 percent being preferred. The same buffer is used for all dilutions. The appropriate antigen, complementary to the specific antibody, is diluted in assay buffer to approximate concentrations to yield about 1 pmole, about 0.1 pmole and about 0.01 pmole of antigen per assay aliquot. Complementary as used herein is defined as the specific antigenic epitope that will specifically bind to an antibody raised specifically against that epitope resulting in an antiepitope antibody. The radioactive probe, $^3$H-labeled compound of formula II complementary to the specific antibody, is diluted in assay buffer to yield about 10,000 cpm per assay aliquot. The assay includes antibody-free samples for determination of non-specific binding, and controls containing antibody and probe without unlabeled antigen, to determine the control level of probe binding. All determinations are made in duplicate.

Following the contacting of the diluted antibody with the labeled probe the mixture is incubated at about 4° C. for about 10 to about 20 hours. Antibody-bound radioactive probe is removed from unbound probe by chromatographic, precipitation, immunoprecipitation or adsorption techniques with adsorption of the unbound probe onto dextran-coated activated charcoal being preferred, as described above. Diluted dextran-coated activated charcoal is added to each sample. After a brief incubation period in a slurry of ice in water, the charcoal is sedimented by centrifugation and the supernatant fluid collected and counted in a $\beta$ counter. The presence of non-labeled antigen inhibits the binding of labeled probe. The inhibition increases as the concentration of non-labeled antigen increases. The extent of inhibition at each level of antigen is calculated as the percent of the specific binding observed in the absence of unlabeled antigen. The sensitivity of antisera are compared by determining for each antiserum the 50% inhibitory concentration ($IC_{50}$) of the specific peptide and then comparing that to the value for the other sera. The $IC_{50}$ as used herein is defined as the concentration of antigen producing 50 percent inhibition of probe binding.

Specificity of the individual antisera is also determined by serologic assays, with RIA being preferred, as described above. The antiserum is diluted in an appropriate buffer, such as assay buffer, to a concentration that binds about 15 percent to about 40 percent of the total radioactive probe, with about 25 percent being preferred. Controls will include probes which do not contain the specific epitope. The radioactive probe, $^{3H}$-labeled antigen complementary to the specific antibody is diluted in assay buffer to yield about 5,000 cpm to about 25,000 cpm with a range of about 10,000 cpm to about 20,000 cpm being preferred per assay aliquot. The volume of each reactant in an assay may range from about 1 ml to about 50 ul, with about 100 ul being preferred. Specificity is determined by either an equilibrium assay or a non-equilibrium assay. In an equilibrium assay the specificity probes are diluted and contacted with a constant amount of antibody and further contacted with a constant amount of complementary labeled probe and incubated for about 10 to about 20 hours. In a non-equilibrium assay the specificity probes are diluted and contacted with a constant amount of antibody and incubated for about 2 to about 20 hours. After the initial incubation, the labeled probe is added and the samples are incubated for a second time for about 30 minutes to about 4 hours. The equilibrium assay is the preferred assay. The assay includes antibody-free controls to evaluate non-specific binding and controls containing antibody and probe without unlabeled antigen to determine the control level of probe binding.

Following the contacting of the antibody and the specificity probe and the subsequent addition of the labeled probe, the mixture is incubated at about 4° C. for about 10 to about 20 hours. Antibody-bound radioactive probe is separated from unbound probe by chromatographic, precipitation, immunoprecipitation or adsorption techniques, with adsorption of the unbound probe onto dextran-coated activated charcoal being preferred, as described above. After a brief incubation period in a slurry of ice in water, the charcoal is sedimented by centrifugation and the supernatant fluid, containing the antibody-bound probe, is collected and counted in a gamma counter. All techniques are known to the art.

The control level of probe binding is determined and the extent of inhibition at each concentration of specificity probe is calculated from the percent of the specific binding observed in the absence of specificity probe. The specificity of each antiserum is measured by comparing the levels of the various specificity probes which yield 50 percent inhibition of labeled probe binding. For a highly specific antiserum, much higher levels of specificity probe than the specific one complementary to the antiserum will be required to yield 50 percent inhibition.

Accordingly, another embodiment of the invention concerns compounds comprising an antigen of formula III

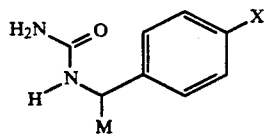

which compound is coupled to a suitable carrier, wherein X is a spacer such as

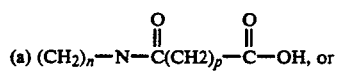

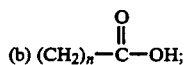

n is 0,1,2,3,4,5 or 6 and p is 0,1,2,3,4,5 or 6.

In one class this embodiment concerns compounds of formula III wherein n is 1, and p is 2.

Compound of Formula III is coupled to the selected carrier by standard procedures well known to those of skill in the art. [See Example 4 and Scheme 3.] As appreciated by those of skill in the art, the spacer includes, but is not limited to substituted bi-phenyl, norleucine, beta-alanine, cysteine, and succinate, wherein the substituent includes $C_{1-6}$ alkyl, $C_{6-10}$ aryl, and $C_{6-10}$ aryl$C_{1-6}$ alkyl. The carrier is typically a high molecular weight protein such as bovine serum albumin (BSA), bovine thyroglobulin (BT), keyhole limpet hemocyanin (KLH), ovalbumin (OA), and the like, with BSA and BT being preferred. Applicants have found it advantageous to couple the compound of Formula III to bovine thyroglobulin as detailed in the Examples Section.

Compounds of formula II are prepared as shown in Schemes 1 and 2. In overview p-tolualdehyde is reacted with lithium bis(trimethylsilyl)amide to form an imine that is further reacted with allyl magnesium chloride. The resulting allyl amine is resolved by fractional crystalization with (1R)-10-camphorsulfonic acid to give (R)-1-amino-1-(p-methylphenyl)-3-butene. The free (R)-amine is regenerated by extraction from a basic aqueous solution and converted to an isocynate with phosgene and subsequently reacted with ammonium hydroxide to form a urea. The allyl double bond is reduced by catalytic hydrogenation to form (R)-α-n-propyl-(4-methylphenyl)methyl urea.

Alternatively, p-hydroxyphenylacetic acid may be converted to the benzofuran ester by alkylation with bromoacetaldehyde diethylacetal followed by hydrolyis of any ester formed, esterification with diazomethane, and cyclization in the presence of polyphosphoric acid. The methyl ester is hydrolyzed to the acid from which the dianion is formed with lithium bis(trimethylsilyl)amide. The dianion is alkylated with allyl bromide and the resulting α-allylphenyl acetic acid resolved by fractional crystalization with (R)-(+)-α-methylbenzylamine. The (R)-acid is converted to the (R)-isocynate by a Curtius rearrangement of the acyl azide. Conversion to the urea is as above.

In a second alternative, p-hydroxyphenylacetic acid can be alkylated with bromoacetaldehyde diethylacetal using sodium hydroxide, followed by esterification with ethanol and sulfuric acid and cyclization in the presence of polyphosphoric acid. In addition the ethyl ester can be alkylated before hydrolysis by sodium hydroxide, in order to reduce the amount of lithium bis(trimethylsilyl)amide used.

Compounds of formula III are prepared as shown in Scheme 3. In overview, methyl (4-methylphenyl)acetate can be alkylated by deprotonation with lithium bis(trimethylsilyl)amide and reaction with an alkyl halide. Bromination of the 4-methyl group can be done with 1,3-dibromo-5,5-dimethylhydantoin or other halogenating agent and the resulting benzylhalide displaced with a nucleophile such as sodium azide. Hydrolysis of the methyl ester results in the substituted acetic acid which can be resolved with R-(+)-α-methylbenzylamine. The free R-acid is regenerated by extraction from aqueous acid solution and converted by a Curtius rearrangement of the acyl azide. The isocynate is converted to the urea as described above. The 4-azidomethyl group is reduced to the 4-aminomethyl which can be acylated with succinic anhydride to afford Compound C.

SCHEME 1
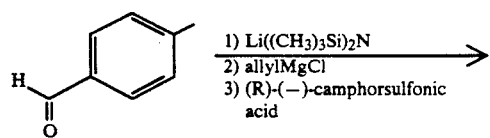
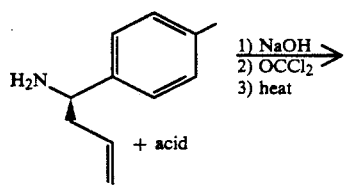
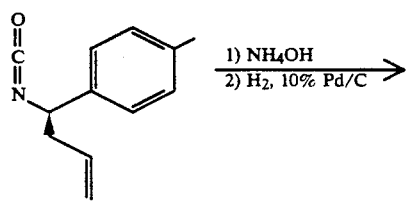
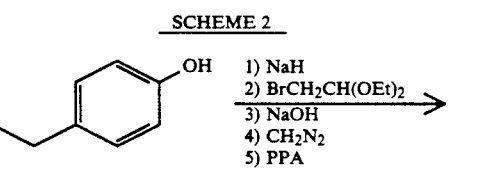
SCHEME 2
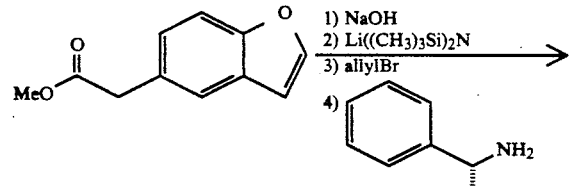
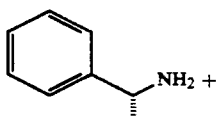
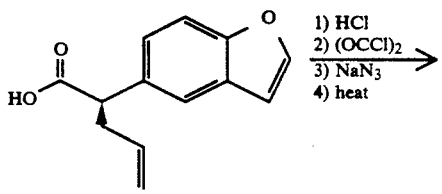
SCHEME 2 -continued
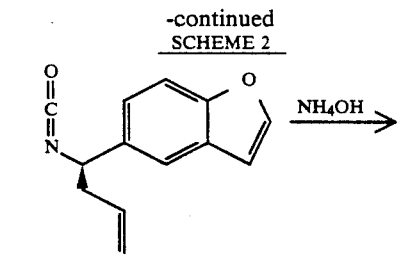
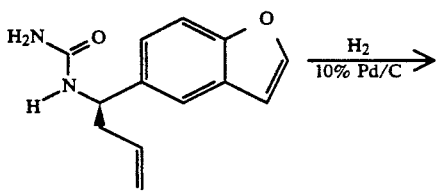
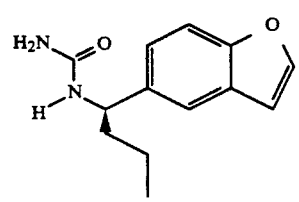
SCHEME 3
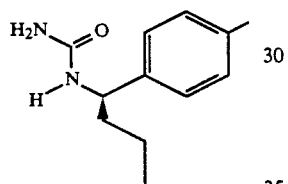
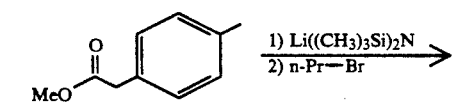
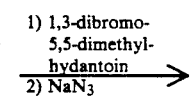
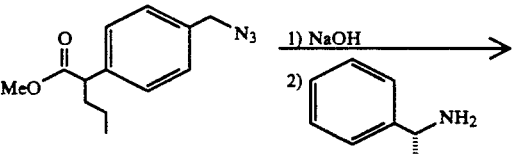
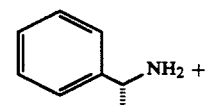
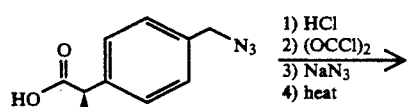
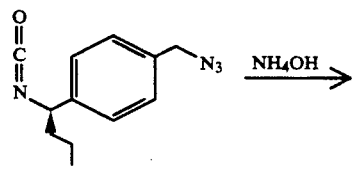

-continued
SCHEME 3

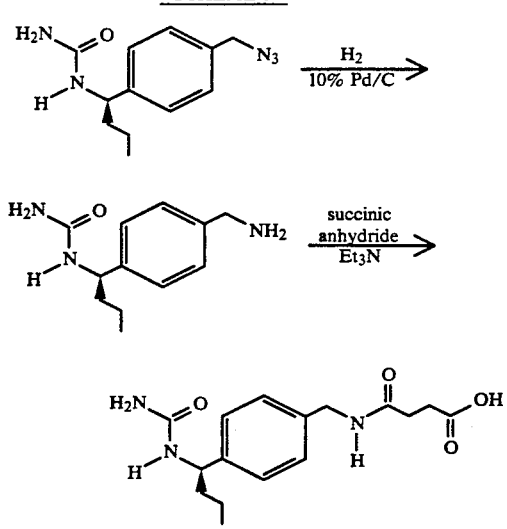

The following examples illustrate the present invention, and as such, are not to be considered as limiting the invention set forth in the claims appended thereto.

EXAMPLE 1

Determination of HLE Inhibited by Compound A

Step A: Blood Incubations

Human heparinized blood was preincubated with various concentrations of Compound A (isobutanolamine salt) for 10 minutes at 37° C. and stimulated for 30 minutes with the calcium ionophore A23187 [CALBIOCHEM CO.] (100 μM) at 37° C. Blood was centrifuged for 10 minutes at 1300×g and platelet rich plasma was removed and extracted as described below.

Step B: Complex

A solution of Compound A (200 μM) and 0.5 μM elastase isolated from human sputum (ATHENS RESEARCH) in 10% dimethyl sulfoxide, phosphate buffered saline (pH 7.3) was incubated by rocking for 30 minutes at room temperature. No elastase activity was measured using the synthetic substrate methoxysuccinyl-Ala-Ala-Pro-Val-pnitroanilide (AAPV).

Step C: Extraction Protocol

Sample (0.5 ml) containing HLE-I complex or inhibitor alone was extracted with 5 ml of water-saturated ethyl acetate, vortexed and centrifuged for 15 minutes at 1300×g. The ethyl acetate phase was discarded and the aqueous sample extracted 2 additional times. Phosphate buffered saline (1.0 ml) was added to each extracted sample (total volume 2 ml) and boiled for 60 minutes. Two ml of acetonitrile were added, the samples vortexed and centrifuged for 15 minutes at 1300×g. The protien pellet was washed with an additional 2 ml of acetonitrile, and the samples vortexed and centrifuged for 15 minutes at 1300×g. The pellet was washed with an additional 2 ml of acetonitrile, the samples vortexed and centrifuged for 15 minutes at 1300×g. The supernatants were combined with the first acetonitrile extraction solutions. The acetonitrile extracts were evaporated to dryness under nitrogen and reconstituted in PET/GEL buffer.

EXAMPLE 2

PRODUCTION OF ANTIBODIES

Antibodies for the reactivation product of formula II were produced by the methods described in Basic methodology of Vituakaitis, Meth. Enzymol. 73: 46–52 (1981). Specifically, New Zealand white rabbits were immunized with Compound C (the para succinyl aminomethyl derivative of compound B'), coupled to thyroglobulin. See Scheme 3. The initial immunizations employed 1 mg of the immunogen conjugate per ml saline homogenized with 1 ml of Freund's complete adjuvant. Rabbits received a total of 0.4 ml divided over 2 intramuscular sites. Animals were boosted 30 days later receiving 0.5 mg immunogen per ml saline homogenized with 1 ml Freund's Incomplete adjuvant. The boost was divided between an intramuscular and a number of subcutaneous sites. Frequent bleeds were taken in order to assess the titer and sensitivity of the antisera. These bleeds were taken ten days after a boost, serum prepared and the serum was frozen and stored at −70° C.

Antibody titer, antibody sensitivity, antibody specificity and the presence of and concentration of reactivation product in body fluids were determined by a radioimmunoassay (RIA). The RIA was carried out in an assay buffer (PET/GEL) containing 50 mM ($CA^{++}$, $MG^{++}$ free) phosphate-buffered saline (GIBCO), 1 mM ethylenedinitrilo-tetraacetic acid (EDTA), 0.01% thimerosal and 0.1% gelitin.

EXAMPLE 3

RADIOIMMUNE ASSAY

Tritium labeled compound A' or B' were used as markers to assess antibody binding. Aliquots (50 μl) of tritium labeled compound B' (35–40,000 dpm/50 μl: Sp. Act. 31 mCi/mmole) or tritium labeled Compound A' (35–40,000 dpm/50 μl: Sp. Act. 278 mCi/mmole) were incubated for 10–20 hr. at 4° C. with 50 μl of the polyclonal rabbit antiserum designated R674 (2nd bleed) diluted 1:3000 in PET/GEL buffer and an additional 100 μl of PET/GEL buffer for a total volume of 200 μl. Non-antibody-bound radioactive isotope was removed from the reaction mixture by it's absorption onto dextran-coated activated charcoal. The dextran-coated activated charcoal was prepared by washing activated charcoal, USP, 3 times with DULBECCO'S phosphate buffered saline (PBS) pH 7.5, and then once with PBS containing 0.25% (w/v) dextran, about 70,000 average mol. wt. The activated charcoal was then suspended to 3% (w/v) in PBS dextran and allowed to stand overnight, washed once again in PBS dextran and resuspended to 3% (w/v) in PBS dextran and stored at 4° C. Immediately before use in the assay, the dextran-coated activated charcoal was diluted 10-fold in DULBECCO's PBS and 1 ml was added to each assay tube. After a 15 minute incubation period at 4° C. the charcoal was sedimented by centrifugation at 1300×g for 15 minutes at 4° C. The supernatant fluid was decanted into 9 ml of AQUASOL-2 scintillation fluid and radioactivity counted in a beta-counter. Each assay contains charcoal free controls, to which 1 ml PBS was added, for determination of total counts (BO), and antibody free controls for determination of non-specific binding. Percent specific binding was determined by subtracting the value for non-specific binding from the value of total antiserum binding and then dividing by the total radioactivity added.

Sensitivity of the antisera R674 (2nd bleed) was determined in the above RIA. The antiserum was diluted in PET/GEL buffer (1:12,000 final dilution in the 200 μl assay volume) as described above so that it binds 20-30% of the total radioactivity added. The same diluted stock was then used for all assay tubes with-in the same assay. The unlabeled reactivation product Compound A' and B' was diluted in PET/GEL buffer to contrations of 20 pmoles, 10 pmoles, 5 pmoles, 2.5 pmoles, 1.25 pmoles, 0.625 pmoles, 0.313 pmoles, 0.156 pmoles and 0.078 pmoles each in a volume of 100 μl. The assay was set up on a competition basis. The unlabeled reactivation product competed with the tritiated reactivation product for binding to the antibody R674. Aliquots of unlabeled reactivation product (100 μl) and aliquots of PET/GEL (100 μl) used for the total radioactivity added, non-specific binding and total binding controls (as described above) were added to 50 μl of tritium labeled compound B' (35–40,000 dpm/50 μl: Sp. Act. 31 mCi/mmole) or tritium labeled compound A' (35–40,000 dpm/50 μl: Sp. Act. 28 mCi/mmole). Following the addition of the diluted antibody R674 (as described above) the assay tubes were incubated for 10–20 hr. at 4° C. Unbound tritiated reactivation product was removed as described above. The presence of unlabeled reactivation product standard competes for or inhibits the binding of the tritiated reactivation product probe. The inhibition increases as the concentration of the unlabeled reactivation product standard increases. The extent of the inhibition at each concentration of reactivation product (B') is calculated as the percent (B/BO) of the specific binding observed in the absence of unlabeled reactivation product standard (BO). The $IC_{50}$ is the concentration of unlabeled reactivation product at which 50% of the tritiated reactivation product binding is inhibited. See FIG. 1.

Samples containing unknown amounts of reactivation product were diluted in PET/GEL the first time to an arbitrary level and 100 μl were incubated with tritiated reactivation product and diluted antibody under the same conditions as described above. The level of inhibition of tritiated reactivation product binding to the antibody was compared with that of known concentrations of unlabeled reactivation product standard to determine the amount of reactivation product in the sample correcting for the dilution made into the PET/GEL buffer. If too much or too little inhibition is seen then the samples were rediluted in PET/GEL appropriately and assayed again.

Figure 2:
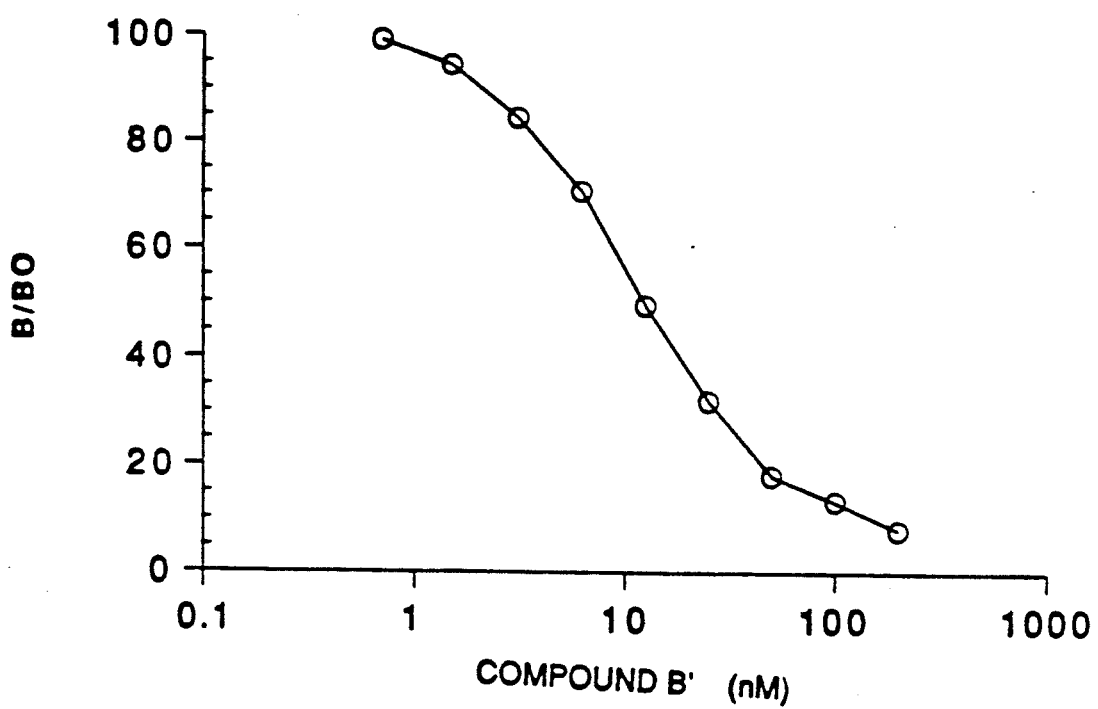
FIG. 2 depicts the binding of Compound B' incubated with $^3$H-Compound B' and antibody R674; total binding (BO) is the number of dpm bound to the antibody in the absence of unlabeled Compound B', and displaced binding (B) is the number of dpm bound to the antibody in the presence of unlabeled Compound B'.

A standard curve showing the displacement of $^3H$-Compound A' with Compound A' as shown in FIG. 1. The $IC_{50}$ was approximately 10 nM and the limit of detection was approximately 2 nM. The displacement by of $^3H$-Compound B' by Compound B' is shown in FIG. 2. The midpoint of this curve was approximately equal to the displacement with Compound A' (10 nM) (FIG. 1). There was no displacement (cross-reactivity) with the free mono-cyclic β-lactam inhibitors. Compounds A and B among others. Urea and arginine were also without affect up to 10 μM (the highest concentration tested).

In FIG. 1 increasing concentrations of Compound A' were incubated with $^3H$-Compound A' and R674 as described in the methods. Total binding (BO) is the number of dpm bound to the antibody in the presence of unlabeled Compound A'.

In FIG. 2 increasing concentrations of Compound B' were incubated with $^3H$-L-Compound B' and R674 as described in the methods. Total binding (BO) is the number of dpm bound to the antibody in the absence of unlabeled Compound B'. Displaced binding (B) is the number of dpm bound to the antibody in the presence of unlabeled Compound B'.

EXAMPLE 4

DISSOCIATION OF HLE-I COMPLEXES

Step A: The production of dissociation products Compound A' and Compound B' in blood Human blood, 1 ml aliquots, was preincubated w Compound B* from 0.01–100 μM for 10 minutes at 37° C. The blood was then incubated for 30 minutes at 37° C. with 100 μM A23187 (CALCHEM CO.) to stimulate the release of HLE from polymorphonuclear leukocytes. Platelet rich plasma was removed from each sample and prepared for the analysis of HLE:$\alpha_1$PI complexes by ELISA, and A$\alpha$(1-21) by specific RIA. The production of the dissociation products Compound A' and Compound B' paralleled the inhibition of A$\alpha$(1-21) by Compound A and Compound B* respectively. Compound A inhibited the formation of HLE:$\alpha_1$PI complexes in a dose dependent manner. The formation of the product Compound A' and Compound B' generated over the concentrations of Compound A and Compound B* used showed a corresponding decrease in the amount of HLE:$\alpha_1$PI complexes made. This data is summarized in Table I. For every mole of dissociation product generated approximately one mole of HLE:$\alpha_1$PI complex is prevented from being formed.

Step B: Removal of free (uncomplexed) compound B

Water-saturated ethyl acetate and acetonitrile were evaluated for use in extracting free unbound inhibitor from that bound to elastase. Plasma was extracted three times with 5 volumes of acetonitrile. After 3 extractions with 5 ml of saturated ethyl acetate, 88 percent of the added complexes was recovered in the aqueous phase, while this procedure removes greater than 99% of unbound free inhibitor into thr ethyl acetate layer.

Step C: Dissociation HLE-I complex

Complexes were made as described above. Five hundred microliters of Compound A' (500 nM), Compound A (200 μM) or complexes containing 200 μM Compound A and 400 nM elastase were added to 0.5 ml of plasma and extracted with the water-saturated ethyl acetate. Samples containing 0.5 ml of 500 nM Compound A' were not extracted. An additional 1 ml of PBS was added to all the samples and the samples were boiled for various times ranging from zero time control up to 3 hours. The boiled plasma samples, including those containing Compound A', were then precipitated and washed with acetonitrile as described below. The conversion of the boiled HLE-Compound complexes to the dissociation product Compound A' was maximum by 30 minutes under neutral conditions. The recovery of the theoretical amount of Compound A' based upon the activity of HLE was 420 pmoles or 105%. Boiled plasma samples containing free uncomplexed Compound A generated concentrations of Compound A' less then the limit of detection in the assay (20 pmoles) confirming that virtually all of the compound was removed during the 3 extractions with water saturated ethyl acetate. The recovery of the 500 pmoles of Compound A' based on weight was approximately 450 pmoles or 90%.

We have shown that the antibody R674 recognizes both dissociation products Compound B' and Compound A' equally as well. We have also demonstrated that R674 does not recognize several β-lactam inhibitors.

EXAMPLE 5

Coupling Of Disassociation Product To Thyrogobulin 1.93 mg of (R)-α-n-propyl-(4-succinylaminoethyl)-phenyl)methyl urea (Compound C) was dissolved in N,N-dimethylformamide (100 ul). 7.2 uMoles of 1-hydroxybenzotriazole monohydrate was then added as well as 9.0 uMoles of dicyclohexylcarbodiimide in dichloromethane. The resulting solution was then stirred for 30 minutes, then 10 mg of bovine thyrogolubin (44 uMoles) in 2.5 ml of degassed 0.1M phosphate buffer, pH 7.6 was then added. After stirring overnight at 4° C. the resulting product was then dialyzed against water (3 changes), and freeze dried.

TABLE I

A23187-STIMULATED BLOOD, PREINCUBATED WITH COMPOUND A AND COMPOUND B*
PRODUCES THE REACTIVATION PRODUCTS COMPOUND A' AND COMPOUND B'
RESPECTIVELY WITH A CORRESPONDING DECREASE IN THE $\alpha_1$PI:ELASTASE COMPLEXES FORMED

| | Concentration Compound A | | |
|---|---|---|---|
| | 1.0 μM | 3.0 μM | 10.0 μM |
| A) pmoles Compound A' | 26.1 | 33.0 | 47.0 |
| B) pmoles of $\alpha_1$PI:Elastase Complexes Displaced | 27.0 | 43.0 | 60.8 |
| B/A | 1.0 | 1.3 | 1.3 |
| | | | Avg. = 1.3 |
| | Concentration Compound B* | | |
| | 0.1 μM | 0.3 μM | 1.0 μM |
| C) pmoles Compound B' | 31.1 | 59.9 | 73.8 |
| D) pmoles of $\alpha_1$PI:Elastase Displaced | 23.0 | 84.3 | 118.5 |
| D/C | 0.7 | 1.4 | 1.6 |
| | | | Avg. = 1.2 |

One ml aliquots of heparinized human blood were incubated for 10 minutes at 37° C. with Compound A or Compound B*. (Compound B* differs from Compound B only by the substituent on the phenoxy.) A23187, 100 μM, was added and the blood was incubated for an additional 30 minutes. The amounts of reactivation product and $\alpha_1$PI:elastase complex in the plasma were determined. The total concentration of $\alpha_1$PI:Elastase complexes formed was 139 μM after treatment with A23187.

EXAMPLE 6

0.083 mM of HLE was incubated for 30 minutes at 25° C. with 0.6 mM Compound B in 0.6 ml of buffer A (450 mM NaCl, 10% DMSO and 45 mM TES at pH 7.5). Excess inhibitor was removed by centrifugal (700×g) gel filtration at 4° C. of 0.5 ml of the solution on 3 ml column of DEAE SEPHADEX A-25 equilibrated in buffer A. Recovery of HLE was 80%. Filtrate containing the compound B derived HLE-inhibitor complex was boiled for 2 hours and then filtered through an AMICON 10,000 molecular weight cutoff filter to remove the protein. 100 ul of the filtrate was diluted with 400 ul eluent A (Acetonitrile:H₂O:methanol, 10:80:10 with 0.1% acetic acid) and injected onto a 4.6×150 mm 5 micron C-18 HPLC column. The column was eluted at the following HPLC conditions;

2 minutes wash with 100% eluant A;
9 minutes gradient to 100% eleant B (Acetonitrile:H₂O:methanol 80:10:10 with 0.1% acetic acid)
9 minutes wash with 100% eluant B
3 minutes gradient to 100% eluant A
4 minutes wash with 100% eluant A.

The product urea, Compound B' elutes at approximately 13.5 minutes. The concentration of urea produced from the enzyme reaction was determined from a standard curve based upon the UV-visible absorbance. In the reaction above, the equivalent of 0.05 mM Compound B' was produced from 0.067 mM HLE-inhibitor complex (75%). The authenticity of the enzyme generated Compound B' was confirmed by mass specteral analysis.

EXAMPLE 7

Following essentialy the same procedure described in EXAMPLE 6, 0.061 mM HLE was incubated with Compound A. After gel filtration, 0.05 mM HLE was recovered. From the HLE-inhibitor complex, 0.0546 mL Compound A' was generated. Compound A' eluted at 14.3 minutes from the HPLC and its identity confirmed by mass spectral analysis.

EXAMPLE 8

(R)-α-n-propyl-(4-methylphenyl)methyl urea, Compound B'

Step A: Preparation of (R)-1-amino-1-(4-methylphenyl)-3-butene, (1R)-(−)-10-camphorsulfonic acid salt A solution of lithium bis(trimethylsilyl)amide was prepared by adding 2.5M n-butyl lithium (208 mL) to a solution of 1,1,1,3,3,3-hexamethyldisilazane (110 mL, 0.52 mol) in tetrahydrofuran (THF) (140 mL) at 0° C. After stirring for 15 min, this solution was added via a cannula to a solution of p-tolualdehyde (59 mL, 0.5 mol) in THF (100 mL), while keeping the temperature between −40° and −50° C. The reaction mixture was then allowed to warm to 10° C. over 30 min. A 2M solution of allyl magnesium chloride (260 mL) in THF was added, keeping the temperature between 10° and 15° C. After stirring for 30 min the reaction was poured into a solution of ammonium chloride (150 gm) in water (1 L). The layers were separated and the aqueous layer was extracted with ether/hexane. The organic layers were washed with brine, combined, dried over sodium sulfate and evaporated. The residue was added to a solution of (1R)-(−)-10-camphorsulfonic acid (62.5 gm) in ethyl acetate (1 L) with cooling. On standing overnight at rt, crystals formed which were filtered and washed with ethyl acetate. The crystals were then stirred with refluxing ethyl acetate (300 mL), filtered and washed with ethyl acetate. The pure title compound weighed 60.7 gm. $[\alpha]_D = -27.16$ (c=0.5, 100% EtOH).

Step B: Preparation of (R)-a-allyl-(4-methylphenyl)-methyl isocyanate

To a slurry of (R)-1-amino-1-(4-methylphenyl)-3-butene, (1R)-(−)-10-camphorsulfonic acid salt (50 gm, 0.122 mol) in ethyl acetate (150 mL) was added 2N sodium hydroxide (75 mL). After all was in solution, the layers were separated and the aqueous layer extracted with ethyl acetate. The combined organic layers were washed with brine, dried over sodium sulfate and evaporated.

A 3-necked flask was fitted with a gas inlet tube, a condenser and an addition funnel without a side arm and charged with ethyl acetate (100 mL). This was heated in a 60° C. oil bath and phosgene bubbled through the solution. A solution of the above free amine in ethyl acetate (20 mL) was added dropwise at a rate such that the white hydrochloride salt did not build up in the reaction mixture. Phosgene was continued to be bubbled in for an additional 5 min after all the amine had been added and the solution was clear. The bath was then heated to 110° C. and the ethyl acetate distilled. The title compound was obtained as a yellow oil (24.99 gm). This was used without purification or could be distilled at 94°-95° C./5 mm. IR 2250 cm$^{-1}$.

Step C: Preparation of (R)-α-allyl-(4-methylphenyl)-methyl urea

To a solution of 7.4N ammonium hydroxide (7.3 mL, 54 mmol) in THF (50 mL) at 0° C. was slowly added over 0.5 hr a solution of (R)-α-allyl-(4-methylphenyl)-methyl isocyanate (5.0 gm, 27 mmol) in THF (50 mL). After 1 hr the reaction was complete by TLC and most of the THF was removed in vacuo. The residue was taken up in ether, washed with water and brine, dried over sodium sulfate and evaporated. The residue was then crystallized from ether/hexanes to give 5.0 gm of white solid. NMR (CDCl$_3$): δ2.34 (s, 3H), 2.50 (br t, 2H, J=7 Hz), 4.4(v br s, 1H), 4.67 (br d, 1H, J=6 Hz), 5.08 (br s, 1H), 5.15 (br d, 1H, J=7 Hz), 5.25 (v br s, 2H), 5.6–5.8 (m, 1H), 7.18 (ABq, 4H, J=9 Hz).

Step D: Preparation of (R)-α-n-propyl-(4-methylphenyl)methyl urea

A solution of (R)-α-n-allyl-(4-methylphenyl)methyl urea (1.15 gm) in 2:1/ethyl acetate:ethanol (50 mL) was hydrogenated over 100 mg 10% Pd/C at 40 psi for 30 min. The reaction was complete at this time by TLC and it was filtered and evaporated. The residue was recrystallized from ethyl acetate to give the title compound as a white solid. mp 153°-155° C. [α]$_D$=+19.9 (c=1.0, CHCl$_3$).

EXAMPLE 9

(R)-α-n-propyl-benzofuran-5-ylmethyl urea

Step A: Preparation of methyl benzofuran-5-ylacetate

A solution of 4-hydroxyphenylacetic acid (20 gm, 0.13 mol) in DMF (50 mL) was slowly added to a suspension of washed sodium hydride (0.26 mol) in DMF (100 mL). Bromoacetaldehyde diethyl acetal (29 mL, 0.195 mol) was then added and the mixture was heated in a 160° C. oil bath for 3 hr. The mixture was then cooled, diluted with water and rendered basic with 2N sodium hydroxide. The mixture was heated to 80° C. for 1 hr to hydrolyze any ester and was then cooled and extracted twice with ether, acidified with 2N hydrochloric acid and extracted twice with more ether. The second ether layers were washed with brine, combined, dried over sodium sulfate and evaporated. The residue was purified by preparative HPLC to afford 8 gm of oil.

This oil was dissolved in ether and excess diazomethane in ether was added. After 15 min the excess diazomethane was destroyed with acetic acid and the mixture was evaporated to an oil.

The above oil was dissolved in benzene (100 mL) and polyphosphoric acid (5 gm) added and the mixture was heated at 90°-100° C. with good mechanical stirring for 3 hr. The reaction was decanted from the dark oil and evaporated. The residue was chromatographed to give 1.3 gm of title compound. NMR (CDCl$_3$): δ3.58-3.83 (m, 5H), 6.74 (dd, 1H), 7.18-7.54(m's, 5H), 7.62 (d, 1H).

Step B: Preparation of benzofuran-5-ylacetic acid

Methyl benzofuran-5-ylacetate (1.2 gm, 6.3 mmol) was dissolved in methanol (10 mL) and 2N sodium hydroxide (6.5 mL) was added under nitrogen and the mixture was stirred at rt for 3 hr. It was then diluted with water and extracted with ether. The aqueous layer was acidified with 2N hydrochloric acid and again extracted twice with ethyl acetate. The organic layers were washed with brine, combined, dried over sodium sulfate and evaporated to give 1.1 gm of title compound suitable for the next step.

Step C: Preparation of (R)-α-allyl-benzofuran-5-ylacetic acid, (R)-α-methylbenzylamine salt A solution of benzofuran-5-ylacetic acid (10.0 gm, 56.76 mmol) in THF (300 mL) was added dropwise over 15 min to a solution of lithium diisopropylamide (120 mmol) in THF at −5° to −10° C. The reaction was stirred at −10° C. for 30 min and then a solution of allyl bromide (10.8 mL, 114 mmol) in THF (20 mL) was added rapidly. The mixture was stirred a further 30 min at −10° C. and then quenched into a mixture of ice water (900 mL), 2N hydrochloric acid (300 mL) and ether (500 mL). The layers were separated and the aqueous layer extracted with another portion of ether. The organic layers were consecutively washed with aqueous sodium bisulfite and brine, combined, dried over sodium sulfate and evaporated. The residue was taken up in isopropanol (250 mL) and (R)-α-methylbenzylamine (5.43 mL, 42.57 mmol) was added and the mixture cooled overnight. The solid salt so obtained was further crystallized several times from isopropanol to give 7.19 gm title salt. [α]$_D$= −24.7 (EtOH)

Step D: Preparation of (R)-α-allyl-benzofuran-5-ylmethyl isocyanate (R)-α-allyl-benzofuran-5-ylacetic acid, (R)-a-methylbenzylamine salt (3.4 gm, 10 mmol) was converted its free acid with 2N hydrochloric acid (10 mL) and extraction with two portions of ether. The combined ether layers were washed with brine, dried and evaporated to give 2.3 gm of oil.

The above free acid was dissolved in benzene (20 mL) and 2 drops of DMF were added followed by oxalyl chloride (1.3 gm, 20 mmol). The reaction was stirred at rt for 30 min and then evaporated to dryness.

The above oil was dissolved in acetone (20 mL) and sodium azide (1.3 gm, 20 mmol) in water (10 mL) was added at 0° C. After 1 hr the reaction was diluted with water and extracted twice with benzene. The organic layers were washed with brine, combined, dried over sodium sulfate and concentrated to about 50 mL without heating. IR 2120 cm$^{-1}$. This solution was then heated to 80° C. for 1 hr and then evaporated to afford 2.2 gm of the title compound as an oil which was used without purification in the next step. IR 2250 cm$^{-1}$.

Step E: Preparation of (R)-α-allyl-benzofuran-5-ylmethyl urea

A solution of crude (R)-α-allyl-benzofuran-5-ylmethyl isocyanate (600 mg) as prepared above in Step D in chloroform (15 mL) was vigorously stirred with 7.4N ammonium hydroxide (1.5 mL) for 30 min. The mixture was then poured into water and extracted twice with methylene chloride. The methylene chloride layers were washed with brine, combined, dried over sodium sulfate and evaporated to give 553 mg of the title compound.

Step F: Preparation of (R)-α-propyl-benzofuran-5-ylmethyl urea

A solution of (R)-α-allyl-benzofuran-5-ylmethyl urea (284 mg) in ethyl acetate (3 mL) was hydrogenated for 5 min over 25 mg of 5% Pd/C at 40 psi and was then filtered and evaporated. The residue was chromatographed eluting with 10% methanol/methylene chloride to obtain 235 mg of the title compound as a white solid. NMR (acetone-$d_6$): δ0.87 (t, 3H, J=7 Hz), 1.2–1.4 (m, 2H), 1.6–1.8 (m, 2H), 4.84 (q, 1H, J=7 Hz), 5.0 (br s, 2H), 6.03 (br d, 1H, J=7 Hz), 6.83 (d, 1H, J=2 Hz), 7.26 (dd, 1H, J=1 Hz, 9 Hz), 7.43 (d, 1H, J=9 Hz), 7.56 (d, 1H, J=2 Hz), 7.77 (d, 1H, J=2 Hz).

EXAMPLE 10

(R)-α-n-propyl-(4-(succinylaminomethyl)phenyl)-methyl urea

Step A: Preparation of (R,S)-methyl 2-(4-methylphenyl)pentanoate

A solution of methyl (4-methylphenyl)acetate (45 gm, 0.27 mol) in THF (500 mL) was cooled to −70° C. in a dry ice bath and 1M lithium bis(trimethylsilyl)amide (290 mL, 0.29 mol) was slowly added maintaining the temperature below −60° C. After 15 min, n-propyl iodide (39.5 mL, 0.40 mol) was added rapidly and the dry ice bath replaced with a water bath. After 30 min at 0° C. the reaction was quenched into a mixture of 2N hydrochloric acid (150 mL) and ice water and extracted twice with ether. The ether layers were successively washed with water and brine containing sodium bisulfite, dried over sodium sulfate and evaporated. The residue was distilled at 85°–90° C./0.2 mm to give 101.5 gm title compound as a clear liquid.

Step B: Preparation of (R,S)-methyl 2-(4-azidomethylphenyl)pentanoate

A suspension of (R,S)-methyl 2-(4-methylphenyl)-pentanoate (5.0 gm, 24.3 mmol) and 1,3-dibromo-5,5-dimethylhydantoin (4.2 gm, 14.6 mmol) in carbon tetrachloride (50 mL) was heated to reflux and benzoyl peroxide was added as needed to initiate the bromination. After 1 hr the reaction was complete and was cooled, filtered and evaporated. The residue was taken up in dimethylformamide (50 mL) and sodium azide (2.4 gm, 36 mmol) was added. The reaction was stirred at rt for 16 hr and then poured into water and extracted twice with ether. The ether layers were washed with brine, dried over sodium sulfate and evaporated. The residue was chromatographed on silica gel eluting with hexanes, then 5% ethyl acetate/hexanes to afford 5.1 gm title compound as an oil. NMR (CDCl$_3$): δ1.92 (t, 3H, J=7 Hz), 1.2–1.4 (m, 2H), 1.65–1.9 (m, 1H), 1.9–2.2 (m, 1H), 3.58 (t, 2H, J=7 Hz), 3.67 (s, 3H), 4.35 (s, 2H), 7.3 (m, 4H). IR 2085 cm$^{-1}$.

Step C: Preparation of (R)-2-(4-azidomethylphenyl)-pentanoic acid, (R)-α-methylbenzylamine salt A solution of (R,S)-methyl 2-(4-azidomethylphenyl)-pentanoate (5.0 gm, 2.0 mmol) and 5N sodium hydroxide (8.0 mL, 40 mmol) in ethanol (50 mL) was heated under nitrogen to 80° C. for 1 hr. The reaction was then cooled, poured into water, acidified with 2N hydrochloric acid and extracted twice with ether. The ether layers were washed with brine, dried over sodium sulfate and evaporated. The residue was taken up in isopropanol (35 mL) and (R)-α-methylbenzylamine (1.5 gm, 12 mmol) was added. The solution was cooled and filtered to give 2.8 gm salt. This was recrystallized twice more from isopropanol to afford 2.2 gm of salt. [α]$_D$= +1.4 (c=1.45, 100% EtOH).

Step D: Preparation of (R)-α-n-propyl-(4-azidomethylphenyl)methyl isocyanate

The salt (2.2 gm, 6.2 mmol) prepared in Example 3, Step C was dissolved in ice water containing 2N hydrochloric acid (6.2 mL) and was extracted twice with ether. The ether layers were washed with a portion of brine, combined, dried over sodium sulfate and evaporated to give 1.5 gm of the free acid as an oil. [α]$_D$= −32 (c=1.57, 100% EtOH).

The above crude acid (1.5 gm, 6.2 mmol) was taken up in methylene chloride (20 mL) and a drop of DMF added. Oxalyl chloride (0.85 mL, 9.3 mmol) was added at rt and the reaction stirred for 1 hr. The volatiles were then removed in vacuo and then under a stream of nitrogen to give the crude acid choloride.

The above acid chloride was taken up in acetone (30 mL) and cooled in an ice bath and a solution of sodium azide (800 mg, 12.4 mmol) in water (20 mL) was added. After 1 hr at 0° C. the reaction was diluted with benzene (50 mL) and the layers separated. The aqueous layer was reextracted with another portion of benzene and the organic layers were washed with brine, combined, dried over sodium sulfate and concentrated in vacuo without heating to about 50 mL. IR 2085 and 2120 cm$^{-1}$. This solution was then heated to 80°–85° C. for 2 hr when IR indicated the reaction was complete to give the title azidomethyl isocyanate, IR 2250 and 2085 cm$^{-1}$. This solution was then evaporated to afford 1.5 gm of the title isocyanate as a crude oil which was used directly in the next step.

Step E: Preparation of (R)-α-n-propyl-(4-azidomethylphenyl)methyl urea

The isocyanate (0.75 gm, 3.0 mmol) prepared in Step D above was dissolved in THF (10 mL) and added over 30 min to an ice bath cooled solution of 7.4N ammonium hydroxide (2.5 mL) in THF (25 mL). After stirring an additional 2 hr, most of the THF was removed in vacuo and the residue taken up in ether, washed with water and brine, dried over sodium sulfate and evaporated. Flash chromatography (100% EtOAc) afforded 460 mg of title urea as a white solid, [α]$_D$= +24 (c=9.2, 100% EtOH).

Step F: Preparation of (R)-α-n-propyl-(4-aminomethylphenyl)methyl urea

A solution of (R)-α-n-propyl-(4-azidomethylphenyl)-methyl urea (460 mg) in ethanol (15 mL) was hydrogenated over 100 mg 10% Pd/C at 40 psi for 3 hr at which time TLC indicated the reaction was complete. The solution was filtered and evaporated. The residue was triturated with ether and dried in vacuo to give 350 mg white solid. NMR (CDCl$_3$): δ1.96 (t, 3H, J=7 Hz), 1.2–1.8 (m, 4H), 3.87 (s, 2H), 4.32 (br s, 2H), 4.57 (q, 1H, J=7 Hz), 4.92 (d, 1H, J=7 Hz), 7.28 (br s, 4H).

Step G: Preparation of (R)-α-n-propyl-(4-(succinylaminomethyl)phenyl)methyl urea To a solution of (R)-α-n-propyl-(4-aminomethylphenyl)methyl urea (250 mg, 1.13 mmol) and triethyl amine (0.32 mL, 2.3 mmol) in methylene chloride (20 mL) was added succinic anhydride (170 mg, 1.7 mmol). The mixture was stirred at rt for 1 hr and was then concentrated in vacuo. The residue was taken up in 15 mL 2N hydrochloric acid and extracted with six portions of ethyl acetate. The organic layers were consecutively washed with a portion of brine, combined, dried over sodium sulfate and evaporated. The residue was flash chromatographed eluting with 1% acetic acid/10% methanol/89% ethyl acetate to afford 200 mg of title compound as a white foam.

What is claimed is:

1. A method for determining the amount of HLE-I complex formed by the association of a β-Lactam inhibitor of formula I with human leukocyte elastase

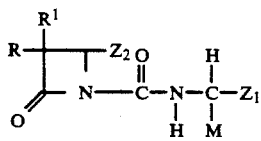

wherein
R and $R^1$ are individually ethyl;
M is allyl or n-propyl,
$Z_1$ is
  (a) 5-benzofuranyl or
  (b) substituted phenyl wherein the substituent is methyl or ethoxy; and
$Z_2$ is substituted phenoxy wherein the substituents are

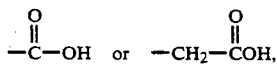

comprising:
(a) obtaining a sample of said HLE-1 complex;
(b) dissociating said HLE-1 complex to yield a product of formula II

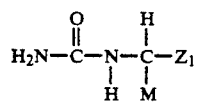

and
(c) determining, quantitatively, the amount of compound of formula II produced.

2. A method according to claim 1, wherein the amount of formula II produced is determined by radioimmunoassay.

3. A method according to claim 2, wherein the dissociation of said HLE-I complex is achieved by heating treating said HLE-I complex.

4. A method according to claim 3, wherein said heat treating of said HLE-I complex is achieved at 37° to 100° C. for 30 to 100 minutes.

5. A method according to claim 4, wherein said heat treating of said HLE-I complex is achieved at pH 5.5 to 7.5.

6. A method for determining the amount of HLE-I complex formed by the association of a β-Lactam inhibitor of formula I with human leukocyte elastase

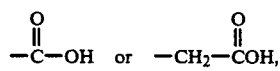

wherein
R and $R^1$ are individually ethyl;
M is allyl or n-propyl,
$Z_1$ is
  (a) 5-benzofuranyl or
  (b) substituted phenyl wherein the subsitituent is methyl or ethoxy; and
$Z_2$ is substituted phenoxy wherein the substituents are

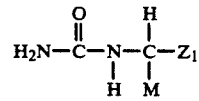

comprising:
(a) obtaining a sample comprising HLE-I association complex;
(b) extracting HLE-I association complex from said sample.
(c) dissociating said HLE-I complex to yield a product of formula II $$H_2N-\overset{O}{\underset{}{C}}-\underset{H}{\overset{H}{N}}-\underset{M}{\overset{}{C}}-Z_1 \qquad II$$

and
(d) determining, quantitatively, the amount of compound of formula II produced.

7. A method according to claim 6, wherein the amount of formula II produced is determined by radioimmunoassay.

8. A method according to claim 7, wherein the dissociation of said HLE-I complex is achieved by heat treating said HLE-I complex.

9. A method according to claim 8, wherein said heat treating of said HLE-I complex is achieved at 37° to 100° C. for 30 to 100 minutes.

10. A method according to claim 9, wherein said heat treating of said HLE-I complex is achieved at pH 5.5 to 7.5.

11. A method according to claim 10 wherein said extraction is conducted with a solvent selected from the group consisting of diethyl ether, ethylene chloride, ethyl acetate, and water saturated ethyl acetate.

12. A method according to claim 11 wherein said extracting is conducted with a solvent which is water saturated ethyl acetate.

* * * * *